United States Patent [19]

Schreiber et al.

[11] Patent Number: 5,362,629

[45] Date of Patent: Nov. 8, 1994

[54] DETECTION OF IMMUNOSUPPRESSANTS

[75] Inventors: Stuart L. Schreiber, Boston, Mass.; Jeffrey S. Friedman, Portola Valley; Irving L. Weissman, Stanford, both of Calif.; Jun Liu, Somerville, Mass.

[73] Assignees: President and Fellows of Harvard College, Cambridge, Mass.; Board of Trustees of the Leland Stanford Junior University, Palo Alto, Calif.

[21] Appl. No.: 740,175

[22] Filed: Aug. 5, 1991

[51] Int. Cl.$^5$ .......... C12Q 1/42; C12Q 1/00; G01N 33/53; A61K 37/02

[52] U.S. Cl. .......... 435/21; 435/7.92; 435/161; 436/161; 514/15; 514/11; 514/885; 530/328; 530/350

[58] Field of Search .......... 435/21, 7.92, 161; 530/328, 350, 827; 514/885, 15, 11; 436/161

[56] References Cited

U.S. PATENT DOCUMENTS

| | | | |
|---|---|---|---|
| 4,722,999 | 2/1988 | Handschumacher et al. | 530/350 |
| 4,740,588 | 4/1988 | Adams et al. | 530/328 |
| 4,778,878 | 10/1988 | Adams et al. | 530/328 |
| 4,997,648 | 3/1991 | Galpin et al. | 514/15 |
| 5,013,719 | 5/1991 | Bowlin | 514/561 |
| 5,047,512 | 9/1991 | Handschumacher et al. | 436/161 |
| 5,079,341 | 1/1992 | Galpin et al. | 530/321 |
| 5,109,112 | 4/1992 | Siekierka et al. | 530/827 |

OTHER PUBLICATIONS

Mattila et al., The EMBO Journal 9:4425–4433 (1990).
Schreiber, Science 251:283–287 (1991).
Dumont J. of Immunology 144:1418–1424 (1990).
Lin et al., Cellular Immunology 133:269–284 (1991).
Kincaid et al., Nature 330:176–178 (1987).
Johansson et al., Transplantation 50:1001–1007 (1990).
Dumont et al., J. of Immunology 144:251–258 (1990).
Bierer et al., Proc. Natl. Acad. Sci. USA 87:9231–9235 (1990).
Bierer et al., Science 250:556–559 (1990).
Tocci et al., J. of Immunology: 718–726 (1989).
Standaert et al., Nature 346:671–674 (1990).
Van Duyne et al., Science 252:839–842 (1991).
Fischer et al., Nature 337:476–478 (1989).
Tropschug et al., Nature 342:953–955 (1989).
Fretz et al., J. Am. Chem. Soc. 113:1409–1411 (1991).
Siekierka et al., Nature 341:755–757 (1989).
Harding et al., Nature 341:758–760 (1989).
Hubbard et al., Biochemistry 28:1868–1874 (1989).
Blumenthal et al., J. of Biological Chemistry 261:8140–8145 (1986).
Moore et al., Nature 351:248–250 (1991).
Handschumacher, Science 226:544–547 (1984).
Kuno, Japanese Journal of Pharmacology Proceedings of 63rd Annual Meeting 5:69P (1990).
Takahashi et al., Nature 337:473–475 (1989).
Heitman et al., Proc. Natl. Acad. Sci. USA 88:1948–1952 (1991).
Michnick et al., Science 252:836–839 (1991).
Sigal et al., J. Exp. Med. 173:619–628 (1991).
Stamnes et al., Cell 65:219–227 (1991).
Klee et al., Biochemistry 17:120–126 (1978).
Klee et al., Proc. Natl. Acad. Sci. USA 76:6270–6273 (1979).
Emmel et al., Science 246:1617–1620 (1989).
Morris, Medline Immunology Today 12:137–140 (1991).
Harding et al; "A receptor for immuno-suppressant FK506 is a cis-trans peptidyl-prolyl isomerase", Nature, vol. (341), pp. 758–760, 1989.
Webster, 9th Edition, p. 690.

*Primary Examiner*—Michael G. Wityshyn
*Assistant Examiner*—Louise N. Leary
*Attorney, Agent, or Firm*—Fish & Richardson

[57] ABSTRACT

A method of evaluating the immunosuppressive activity of a compound including contacting the compound with calcineurin and determining the ability of the compound to bind to the calcineurin. The ability to bind to the calcineurin is positively correlated to the immunosuppressive activity of the compound.

1 Claim, No Drawings

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 19
        ( B ) TYPE: amino acid
        ( C ) STRANDEDNESS:
        ( D ) TOPOLOGY: linear ( x i ) SEQUENCE DESCRIPTION: SEQ ID NO: 1:

Asp Leu Asp Val Pro Ile Pro Gly Arg Phe Asp Arg Arg Val Ser Val
                5                          10                        15

Ala Ala Glu
      19

( 2 ) INFORMATION FOR SEQ ID NO: 2:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 2:

CAGGACACAG GATCCATGGG CGTGCAGGTG GA                      32

( 2 ) INFORMATION FOR SEQ ID NO: 3:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( x i ) SEQUENCE DESCRIPTION: SEQ ID NO: 3:

GCTGGCTAAC GAATTCAAGG GAGGAGGCCA TTCCTGTCAT          40

( 2 ) INFORMATION FOR SEQ ID NO: 4:

( i ) SEQUENCE CHARACTERISTICS:
        ( A ) LENGTH: 25
        ( B ) TYPE: amino acid
        ( C ) STRANDEDNESS:
        ( D ) TOPOLOGY: linear ( x i ) SEQUENCE DESCRIPTION: SEQ ID NO: 4:

Ser Gln Thr Thr Gly Phe Pro Ser Leu Ile Thr Ile Phe Ser Ala Pro
                5                          10                       15

Asn Tyr Leu Asp Val Tyr Asn Asn Lys
        20                25

(2) INFORMATION FOR SEQ ID NO: 5:

(i) SEQUENCE CHARACTERISTICS:
        (A) LENGTH: 20
        (B) TYPE: amino acid
        (C) STRANDEDNESS:
        (D) TOPOLOGY: linear (xi) SEQUENCE DESCRIPTION: SEQ ID NO: 5:

Ile Tyr Asp Met Asp Lys Asp Gly Tyr Ile Ser Asn Gly Glu Leu Phe
            5                      10                  15

Gln Val Leu Lys
      20

DETECTION OF IMMUNOSUPPRESSANTS

This invention was made in the course of work supported by the United States Government, which has certain rights in the invention.

BACKGROUND OF THE INVENTION

This invention relates to agents which decrease the immune response, i.e., immunosuppressive agents.

Cyclosporin A (CsA), a cyclic undecapeptide of fungal origin, and FK506, a neutral macrolide of fungal origin, are potent immunosuppressants. Despite their lack of structural similarities, CsA and FK506 have similar biological properties (Johansson et al., 1990, Transplant. 50:1001; Lin et al., 1991, Cellular Immunol. 133:269). Both molecules interfere with a T-cell receptor-mediated signaling pathway that results in the transcription of early T cell activation genes, although FK506 is able to do so at 100-fold lower concentrations (Tocci et al., 1989, J. Immunol. 143:718).

SUMMARY OF THE INVENTION

In general, the invention features a method of evaluating the immunosuppressive activity of a compound or agent. The method includes: contacting the compound or agent with calcineurin and determining the ability of the compound or agent to bind to the calcineurin, the ability to bind to the calcineurin being positively correlated to the immunosuppressive activity of the compound or agent.

In another aspect, the invention features a method of evaluating the immunosuppressive activity of a compound or agent. The method includes contacting the compound or agent with calcineurin and determining the ability of the compound or agent to modulate the phosphatase activity of the calcineurin, the ability to modulate, e.g., decrease, the phosphatase activity of the calcineurin being correlated to the immunosuppressant activity of the compound or agent.

In preferred embodiments the determination of the ability of the compound or agent to modulate the phosphatase activity includes contacting the compound (or agent)-contacted-calcineurin with a substrate and determining the ability of the compound (or agent)-contacted-calcineurin to dephosphorylate the substrate as compared to the ability of calcineurin which has not been contacted with the compound or agent to dephosphorylate the substrate.

In another aspect, the invention features a method of isolating an immunosuppressive compound or agent. The method includes contacting the compound or agent with calcineurin, allowing the compound or agent to form an affinity complex with calcineurin, and isolating said compound or agent by its affinity for calcineurin.

In another aspect the invention features a method of evaluating the immunosuppressive activity of a compound or agent. The method includes: contacting the compound agent with an immunophilin, e.g., a cyclophilin or an FKBP, and allowing a complex including the compound or agent and the immunophilin to form; contacting the complex with calcineurin; and determining the ability of the complex to bind to the calcineurin. The ability to bind to the calcineurin is positively correlated to the immunosuppressive activity of the compound or agent.

In preferred embodiments the method includes contacting the calcineurin with calmodulin prior to determining the ability of the complex to bind to the calcineurin.

In another aspect, the invention features a method of evaluating the immunosuppressive activity of a compound or agent. The method includes: contacting the compound or agent with an immunophilin and allowing a complex including the compound or agent and the immunophilin to form; contacting the complex with calcineurin; contacting the calcineurin with a substrate; and determining the ability of the calcineurin to dephosphorylate the substrate. The ability to dephosphorylate the substrate is correlated, e.g., inversely correlated, to the immunosuppressant activity of the compound or agent.

In preferred embodiments the method includes contacting the calcineurin with calmodulin prior to determining the ability of the calcineurin to dephosphorylate the substrate.

In another aspect the invention features a method of evaluating the immunophilin-activity of a compound. The method includes: contacting the compound with an immunosuppressive agent, e.g., cyclosporin or FK506, and allowing a complex including the compound and the immunosuppressive agent to form; contacting the complex with calcineurin; and determining the ability of the complex to bind calcineurin. The ability is positively correlated with immunophilin-activity.

In preferred embodiments the method includes: contacting the calcineurin with calmodulin prior to determining the ability of the complex to bind calcineurin.

In another aspect the invention features a method of evaluating the immunophilin-activity of a compound. The method includes: contacting the compound with an immunosuppressive agent, e.g., cyclosporin or FK506, and allowing a complex including the compound and the immunosuppressive agent to form; contacting the complex with calcineurin; contacting the calcineurin with a substrate; and determining the ability of the calcineurin to dephosphorylate the substrate. The ability to dephosphorylate the substrate is correlated, e.g., inversely correlated, to the immunophilin-activity of the compound.

In preferred embodiments the method includes contacting the calcineurin with calmodulin prior to determining the ability of the calcineurin to dephosphorylate the substrate.

In another aspect the inventor features a method for isolating an immunosuppressive compound or agent from a sample. The method includes: contacting the sample with an immunophilin, e.g., a cyclophilin or an FKBP, and allowing a complex to form between the immunophilin and the immunosuppressive compound or agent; and contacting the complex with calcineurin to allow the complex to form an affinity complex with calcineurin.

In preferred embodiments the method includes contacting the calcineurin with calmodulin prior to contacting the complex with calcineurin.

In another aspect the invention features a method for isolating an immunophilin from a sample. The method includes: contacting the sample with an immunosuppressive agent, e.g., CsA or FK506, and allowing a complex to form between the immunophilin and the immunosuppressive agent; and contacting the complex with calcineurin to allow the complex to form an affinity complex with calcineurin.

In preferred embodiments the method includes contacting the calcineurin with calmodulin prior to allowing the affinity complex to form.

In another aspect the invention features a method for isolating a complex including an immunosuppressive agent, e.g., CsA or FK506, and an immunophilin, e.g., an FKBP or a cyclophilin, from a sample. The method includes: contacting the complex with calcineurin; and isolating the complex by its affinity for calcineurin.

In preferred embodiments the method includes contacting the calcineurin with calmodulin prior to isolating the complex.

The invention also includes a: purified preparation of an affinity complex of calcineurin, an immunophilin, e.g., a cyclophilin or an FKBP, and an immunosuppressant, e.g., CsA or FK506; an immunophilin isolated by the methods described herein; an immunosuppressant isolated by the methods described herein; and an affinity complex including an immunophilin and an immunosuppressant isolated by the methods described herein.

In another aspect the invention features a method of treating an animal, e.g., a human, afflicted with a condition characterized by an inhibited or weakened immune response. The method includes increasing the dephosphorylation, preferrably the calcineurin-mediated dephosphorylation, of a substrate which is normally dephosphorylated by calcineurin, e.g., by administering calcineurin.

In another aspect, the invention features a method of treating an animal, e.g., a human, afflicted with a condition characterized by an unwanted immune response, e.g., an autoimmune disease; a cell growth related disorder, e.g., cancer; or transplant rejection. The method includes inhibiting the dephosphorylation of a substrate which is normally dephosphorylated by calcineurin, by administering an effective amount of a selected immunosuppressive compound or agent.

In another aspect, the invention features a method of isolating calcineurin from a sample. The method includes contacting the sample with an immunosupressive compound, or, with a complex including, essentially, an immunophilin, e.g., a cyclophilin or an FKBP, and an immunosuppressive agent, e.g., cyclosporine A or FK506, and isolating calcineurin by its affinity for the compound or the complex.

Immunophilin, as used herein, refers to a molecule capable of forming a complex with an immunosuppressive drug. The complex has greater in vivo or in vitro immunosuppressive activity than does either of the uncomplexed components.

Cyclophilin, as used herein, refers to an immunophilin which complexes with cyclosporine A.

Immunosuppressive agent, or drug, or immunosuppressant, as used herein, refers to a substance which can complex with an immunophilin and which can suppress or weaken the immune response. An immunosuppressive drug complexed with an immunophilin has greater in vivo or in vitro immunosuppressive activity than when in the uncomplexed state.

An immunosuppressive compound, as used herein refers to a substance which can suppress or weaken the immune response, preferrably through an interaction with calcineurin, but which is not necessarily capable of forming a complex with an immunophilin.

Calcineurin, as used herein, refers to any fragment or analog of calcineurin A, calcineurin B, or both, which is capable of complexing with an immunosuppressant-immunophilin complex, e.g., with a FK506/FKBP complex or a CsA/cyclophilin complex.

Complex or affinity complex, as used herein, refers to an association of a receptor and its ligand. The association can include either or both covalent and noncovalent bonds. Immunosuppressive, as used herein, refers to the ability to weaken the immune response.

Immunophilin activity, as used herein, refers to the ability to complex an immunosuppressant and preferably to increase the immunosuppressive activity of the complexed immunosuppressant.

Purified preparation of a substance, as used herein, refers to a preparation which is at least 10% and more preferably at least 50%, 75%, or 90% by weight, preferably dry weight, the substance.

A selected immunosuppressive compound or agent, as used herein, refers to an immunosuppresive compound or agent, other than cyclosporine A or FK506, which inhibits the dephosphorylation of a substrate which is normally dephosphorylated by calcineurin. Preferrably, the selected immunosuppressive compound or agent is isolated by the methods described herein.

The inventors have discovered that complexes between structurally diverse immunosuppressants and their respective immunophilins, e.g., the cyclophilin-A-CsA complex and the FKBP-12 FK506 complex, bind to and inhibit the activity of a common cellular target, the calcium-calmodulin dependent phosphatase calcineurin (also known as PP2B).

The methods and compounds of the invention are useful in the following: the identification of and isolation of immunosuppressive agents; the identification of and isolation of substances, e.g., immunophilins, involved in the immune response; the elucidation of mechanisms of action in the immune response; the suppression of the immune response; and in the treatment of conditions, e.g., AIDS, characterized by a weakened immune response.

Other advantages and features will become apparent from the following descriptions and from the claims.

DETAILED DESCRIPTION

Immunosuppressive Agent-Immunophilin Complexes Bind to Calcineurin and Inhibit its Phosphatase Activity The experiments described below demonstrate the in vitro binding of a human cyclophilin A-CsA complex and a human FKBP12-FK506 complex to a common cellular target, which is not bound by cyclophilin A, FKBP12, FKBP12-rapamycin, or FKBP12-506BD. The target is a complex of 61 kDa calcineurin A, 19 kDa calcineurin B (collectively referred to as calcineurin, which is a $Ca^{2+}$, calmodulin-dependent serine/threonine-phosphatase (Klee et al., 1978, Biochemistry 7:1205; Klee et al., 1979, Proc. Natl. Acad. Sci USA 76:6270; Stewart et al., 1982, FEBS Lett. 137:80) and calmodulin. Calcineurin was found to meet the biochemical requirements of the common target of immunosuppressive agent-immunophilin complexes and thus of a component of T-cell receptor-(TCR) and IgE receptor-signaling pathways involved in transcription and exocytosis.

As shown in Experiment 3 below, proteins of $M_r$ 61,000, 57,000, 17,000, and 15,000 from calf thymus were retained on FKBP 12-based affinity matrices only when the affinity matrices had been preloaded with FK506. Affinity matrices based on FKBP12, FKBP12- rapamycin, CsA, FK506, and rapamycin do not retain any of these proteins. The 17-kDa protein was identified as calmodulin, the 61-kDa and 57-kDa proteins as calcineurin A, and the 15-kDa protein as calcineurin B, as shown in Experiment 6 below.

Calcineurin is a $Ca^{2+}$, calmodulin-dependent serine-/threonine phosphatase previously shown to be the predominant calmodulin-binding protein in T lymphocytes (Kincaid et al., 1987, Nature 330:176). The gel mobilities on SDS-PAGE reported for calcineurin-A (61 kDa), calcineurin-B (19 kDa, $M_r$ 15,000 on SDS-PAGE), and calmodulin (17 kDa) and the proteins described above are the same as described above. Furthermore, calcineurin-A has been reported to undergo a facile proteolytic cleavage of a C-terminal peptide to yield a 57 kDa fragment (Hubbard et al., 1989, Biochemistry 28:1868). Treatment of the eluted proteins with $Ca^{2+}$ prior to gel electrophoresis resulted in a gel mobility shift for the $M_r$ 15,000 and 17,000 bands that are characteristic of myristoylated calcineurin-B and calmodulin (Klee et al., 1979, Proc. Natl. Acad. Sci. USA 76:6270), respectively. Blotting experiments with anti-calcineurin antibodies and $^{45}Ca^{2+}$, provide further support for the identification of the $M_r$ 61,000, 57,000, 17,000, and 15,000 bands as calcineurin-A, the C-terminal peptide cleavage product of calcineurin-A, calmodulin, and calcineurin-B, respectively.

Elution of the proteins from the immunosuppressive agent-immunophilin matrix was achieved with soluble cyclophilin-A-CsA or FKBP-12-FK506 complexes, as shown in Experiment 3 below. These results suggest the two immunosuppressive agent-immunophilin complexes bind to the common target competitively. The sensitivity of $Ca^{2+}$-dependant signaling pathways to both CsA and FK506 is probably related to the finding that a calcium chelator, EGTA, is able to effectively elute the four proteins, as shown in Experiment 4 below.

The primary immunosuppressive agent-immunophilin interaction site within the target calcineurin-calmodulin complex was shown, in Experiment 6 below, to reside within calcineurin by affinity experiments with calcineurin samples that lacked calmodulin. In these experiments, only the cyclophilin-CsA and FKBP-FK506 matrices were able to retain purified calcineurin, as described below.

The phosphatase inhibition studies described in Experiment 6 below confirm the identity of calcineurin as the primary site of interaction. The influence of immunophilins or immunophilin-drug complexes on the phosphatase activity of calcineurin in the presence of $Ca^{2+}$ and calmodulin was assayed with both paranitrophenyl phosphate and a phosphopeptide substrate ($H_2N$-Asp-Leu-Asp-Val-Pro-Ile-Pro-Gly-Arg-Phe-Asp-Arg-Arg-Val-Ser-($OPO_3^{2-}$)Val-Ala-Ala-Glu-$CO_2H$) (Sequence I.D. No. 1). In accord with the binding studies, a specific effect is seen with the complexes of both cyclophilin-A-CsA and FKBP-12-FK506. Whereas these complexes induce a slight increase in the phosphatase activity of calcineurin-$Ca^{2+}$/calmodulin (by a factor of ca. 2–3) towards para-nitrophenyl phosphate, they potently inhibit activity towards the phosphopeptide substrate in the presence or absence of calmodulin. These results suggest that the biological function of the immunophilin-drug complexes may be to inhibit phosphatase activity of calcineurin, but that this may be achieved by binding to a site adjacent to the active site, rather than to the active site. The small para-nitrophenyl phosphate reagent presumably interacts with calcineurin nearly exclusively via active site residues, whereas the phosphopeptide, which is comprised of a sequence derived from the phosphorylation site on the RII subunit of cyclic AMP-dependent protein kinase (a calcineurin substrate) (Blumenthal et al., 1986, J. Biol. Chem 261:8140), is presumed to make extensive contact with the enzyme. In both phosphatase assays, no effect was observed with cyclophilin- A, FKBP-12, CsA, FK506, or rapamycin alone, or with the FKBP 12-rapamycin and FKBP12-506BD complexes.

These biological investigations suggest the calcium-/calmodulin dependent phosphatase calcineurin is the common "downstream" biological target of CsA and FK506. As these agents exhibit specificity for activation pathways that induce an increase in intracellular $Ca^{2+}$-concentration, such as those mediated by the TCR and IgE receptor, calcineurin may be involved in regulating the phosphorylation state of a downstream component of these signaling pathways. This model is able to reconcile the effects of CsA and FK506 on the disparate processes of exocytosis and transcription. For example, dephosphorylation of a cytoplasmic transcription factor-anchor protein complex would initiate nuclear translocation of the cytoplasmic unit of a transcription factor (e.g., NF-AT) resulting in transcription, whereas dephosphorylation of a "secretory vesicle transport protein" (e.g., synapsin I) would initiate exocytosis. The cellular specificity of the actions of CsA and FK506 may be related to their selective interactions with specific isoforms of calcineurin or due to the existence of cell-specific calcineurin substrates.

The identification of a common phosphatase target of cyclophilin A-CsA and FKBP12-FK506 complexes also provides support for the hypothesis that immunophilin-ligand complexes are the agents responsible for inhibition of cytoplasmic signaling. In this model, the immunophilin is not necessarily a component of the signaling pathway—its role in the uncomplexed state is not specified. Only upon complexation with its immunosuppressive ligand is an inhibitory complex formed.

CsA and FK506 appear to exhibit a novel mechanism of action. These molecules apparently "hijack" constitutively expressed cellular proteins to form an inhibitory complex that further interacts with a component of the signal transduction pathway to form a ternary complex. The ability of the immunosuppressants to bring together two proteins is reminiscent of the role of antigenic peptides, which mediate the binding of MHC molecules to the polymorphic TCRs. Especially interesting in this regard is the apparent ability of FKBP12 to present two ligands (FK506 and rapamycin) to distinct cellular targets.

As cyclophilin A is the predominant T cell and mast cell cyclophilin isoform, and is found in the cytosol, it appears that it is primarily responsible for mediating the actions of CsA in these cell lines. Other cyclophilin isoforms may mediate the actions of CsA analogs that bind weakly to cyclophilin A, yet have potent immunosuppressive activity. Although it is possible that these analogs may bind directly to calcineurin without the need for presentation by cyclophilins, a more likely possibility is that the complexes of cyclophilin A with these CsA analogs may bind to calcineurin with increased affinity (relative to the cyclophilin A-CsA complex). FK506 analogs with analogous properties may be analyzed in a similar matter.

The competitive binding of cyclophilin A-CsA and FKBP12-FK506 to calcineurin is interesting in light of the absence of apparent structural similarities between the immunophilins cyclophilin A and FKBP12, and their ligands CsA and FK506. It is possible that different binding elements within the same binding site on calcineurincalmodulin are used by these direct immunophilin-drug complexes.

Experiment 1

Construction of a Glutathione S-Transferase-FKBP12 fusion protein

To facilitate the expression, purification, and solid state immobilization of FKBP12, a fusion of FKBP12 encoding DNA to glutathione S-transferase encoding DNA was made. (Early binding studies involved covalently derivatized (e.g., biotinylated) immunophilins used in the context of ligand blotting, expression screening, and affinity chromatography techniques. The covalent modification of FKBP12 resulted, however, in significant reduction in drug affinity.)

A chimeric gene encoding glutathione S-transferase-FKBP12 fusion protein (GFK) was constructed by fusing the cDNA encoding FKBP12 (Standaert et al., 1990, Nature 346:671, hereby incorporated by reference) to the DNA encoding carboxyl terminus of glutathione S-transferase (Smith et al., 1988, Gene 67:31, hereby incorporated by reference). FKBP12 was amplified by PCR from an FKBP12 coding plasmid (pRFS) (Standeart et al., 1990, supra) using two primers: 5' primer, 5'-CAGGACACAGGATCCATGGGCGT-GCAGGTGGA-3' (Sequence I.D. No. 2); 3' primer, 5'-GCTGGCTAACGAATTCAAGGGAGGAGG-CCATTCCTGTCAT-3' (Sequence I.D. No. 3). The PCR fragment was purified by phenol-chloroform extraction and ethanol precipitation. It was then digested with EcoRI and BamHI and cloned into pGEX-2T (Smith et al., 1988, Supra), which had been linearized with the same restriction enzymes. The fusion construct, pGFK12, was transformed into E. coli XA90 (G.L. Verdine, Harvard University ) in which the expression of GFK can be induced with isopropyl-$\beta$-D-thiogalactopyranoside (IPTG).

Experiment 2

Purification of the GKF Fusion Protein

After transformation of the resulting construct pGFK12 into E. coli XA90, induction with IPTG yielded the fusion protein GFK as the major constituent of soluble, cellular proteins. GFK was partially purified by ammonium sulfate fractionation (40–80%), glutathione affinity chromatography, and DE 52 anion exchange chromatography. The purification was performed as follows. A 1 liter LB culture of XA90/pGFK12 was incubated at 37° C. At an $OD_{595}$ of 0.65, the culture was induced with 1 mM IPTG. The cells were harvested 6h after induction, resuspended in 20 mL of 20 mM Tris HCl (pH 7.8) with 1 mM PMSF, and lysed by two passes through a French press at 12,000 psi. The nucleic acids were precipitated by addition of one fifth volume of neutralized 2% protamine sulfate solution to the crude lysate followed by centrifugation (20,000×g, 20 min.). The crude cell extract was then fractionated with ammonium sulfate and the 40–80% protein pellet was resuspended in 30 mL of 20 mM TrisHCl (pH 7.8) and dialyzed against 4 liters of the same buffer.

The dialyzed protein solution was first purified with glutathione Sepharose as described previously (Smith et al. 1988, supra). The glutathione (5 mM) eluent from the glutathione sepharose affinity column was directly loaded onto a DE 52 column that had been equilibrated with 5 column volumes of 20 mM TrisHCl (pH 7.8). The column was then washed with another 5 column volumes of the buffer and the fusion protein was eluted with a step gradient of 0–200 mM KCl. GFK-containing fractions were collected and used directly.

GFK fractions after DE 52 chromatography were nearly homogeneous as judged by Coomassie blue staining. However, several other protein bands were visible with silver stain.

The rotamase activity of GFK and its ability to be inhibited by FK506 and rapamycin were determined in the presence and absence of reduced glutathione. GFK has rotamase activity and affinities for FK506 and rapamycin similar to those of recombinant human FKBP12; furthermore, neither its rotamase activity nor affinities for the drugs are affected by the presence of glutathione. Thus, it appears that immunophilin and glutathione S-transferase domains act independently in the fusion protein.

Experiment 3

A Common Set of Proteins Bind to Cyclophilin-CsA and FKBP-FK506, but not Cyclophilin, FKBP, CsA, FK506, Rapamycin, or FKBP-Rapamycin Several factors were taken into account in the design of the first glutathione-Sepharose adsorption experiment. Since both CsA and FK506 inhibit $Ca^{2+}$-dependent signaling pathways, $Ca^{2+}$ and $Mg^{2+}$ were included in the incubation buffer (see below). In addition, in some experiments, a homobifunctional cross-linking reagent, dimethyl 3,3'-dithiobispropionimidate (DTBP) (Wang et al. 1974, J. Biol. Chem. 249:8005) was added to the incubation mixture to retain target proteins whose affinity for immunophilin or immunophilin-drug complex was not sufficient to withstand the washes following adsorption of the complex to the solid phase. Under these conditions, four proteins of $M_r$ 61,000, 57,000, 17,000, and 15,000 from calf thymus extract were found to be specifically adsorbed by the GFK-FK506 complex but not by GFK alone or the GFK-rapamycin complex. Subsequently, it was found that the affinity of these four proteins for GFK-FK506 was sufficiently high that the cross-linking reagent was not necessary. Furthermore, the same set of proteins was detected in other tissues such as bovine brain and spleen, with brain being the most reliable source.

Adsorption of calcineurin-calmodulin with GFK-FK506 using glutathione Sepharose was performed as follows. Crude tissue extracts, fresh bovine calf brain, thymus, or spleen (Research 87, Revere, MA), were homogenized (1:3 W/V) in 20 mM Tris HCl (pH 6.8), 0.25 mM NaCl, 2 mM $\beta$-mercaptoethanal, 0.02% $NaN_3$, 1 mM PMSF, and 5% glycerol. The homogenate was centrifuged at 8,000×g for 4 h. The supernatant was separated and the pellet was resuspended in an equal volume of the same buffer. Centrifugation at 8,000 ×g for 4 h gave a second supernatant. The two supernatants were mixed (1:1 v/v) and centrifuged at 30,000×g for 45 min. The supernatant was then filtered through a 0.45 μm filter and kept at 4° C. before use.

The crude tissue extracts were pre-incubated with glutathione Sepharose (about 1:100 to 1:200 dilution of the sepharose) at 4° C. for 1–3 h to remove the endogenous glutathione binding proteins, including glutathione S-transferases. A typical incubation mixture had a total volume of 0.2 mL consisting of buffer A (50 mM Tris HCl (pH 7.5), 100 mM NaCl, 2 mM $MgCl_2$, 2 mM $CaCl_2$), 2 μM GFK, 20 μM FK506 (or rapamycin or CsA) and 0.05 to 0.1 mL tissue extracts. After incubation at 4° C. on a nutator for 1.5 h, 25 μL of 50% (V/V) glutathione Sepharose in buffer A was added and incubation was continued for an additional 0.5 to 2 h. The Sepharose beads were precipitated by centrifugation on a microcentrifuge at $5,000 \times g$ for 2 min. The glutathione Sepharose beads were washed three times with 0.5 mL buffer A containing 0.2% Triton X-100. The washed glutathione Sepharose was then resuspended in 25 μL of 2× SDS sample buffer, heated in boiling water for 3 min, and centrifuged for 2 min. The supernatant was subjected to SDS-PAGE followed by silver staining. For purification of the target proteins from calf thymus and brain extracts, each of the components was scaled up proportionally and the proteins were eluted with 20 mM EGTA in 50 mM Tris-HCl, pH 7.4 and 1 mM dithiothreitol after three washes with buffer A containing 0.2% Triton X-100.

Competitive binding experiments showed that both GFK-FK506 and cyclophilin A-CsA bind to the same set of proteins. A competitive binding experiment was carried out with recombinant FKBP12 and cyclophilin A (Standaert et al., 1990, supra, Lui et al., 1990, Proc. Natl. Acad. Sci. 87:2304) and their respective drug complexes. After the set of four target proteins were adsorbed onto the glutathione Sepharose affinity matrix, elution was attempted with immunophilins, the drugs, or the immunophilin-drug complexes. The set of four proteins were eluted from glutathione-sepharose immobilized GFK-FK506 with both recombinant complexes. In contrast, these proteins were not eluted by free immunophilins or unbound drugs. In addition, the FKBP12-rapamycin complex did not elute the target proteins, in agreement with previous observation.

Experiment 4

Divalent Metal Ion-Dependence of Immunophilin-Drug/Target Protein Complex Formation and Purification of the Target Proteins by EGTA Elution When $Ca^{2+}$ and $Mg^{2+}$ were accidentally omitted from the incubation buffer, no target proteins were retained by GFK-FK506. To further test the importance of divalent metal ions for interaction between immunophilin-drug complexes and target proteins, the adsorption experiment was performed in the presence of the $Ca^{2+}$ chelator EGTA. GFK-FK506 complexes no longer retained the target proteins when EGTA was present. In addition, EGTA was found to be capable of eluting the four proteins from the GFK-FK506 complex immobilized on glutathione sepharose without a significant effect on the interactions between GFK and glutathione sepharose. This proved to be an effective way of purifying the target proteins.

GFK-FK506 bound to glutathione Sepharose matrix was loaded with calf thymus extract and eluted with EGTA. Two contaminant proteins were seen to coelute with the four target proteins, the 38kDa GFK and a less abundant $M_r$ 26,000 protein that may be a glutathione S-transferase either from the proteolytic cleavage of GFK or from the calf thymus extract. With this procedure, over 40 μg of proteins can be purified from 20 mL of calf thymus extract (120 mg of protein).

Experiment 5

Identification of the 17-kDa Protein as Calmodulin, the 61-kDa and 57-dDa Proteins as Calcineurin A, and the 15-kDa Protein as Calcineurin B The metal ion-dependency (especially $Ca^{2+}$-dependency) binding of the target proteins to the immunophilin-drug complexes supported the possibility that the $M_r$ 17,000 protein was calmodulin. One of the distinctive properties of calmodulin is its $Ca^{2+}$-dependant gel mobility shift, i.e., calmodulin migrates faster in the presence of $Ca^{2+}$ during SDS-polyacrylamide gel electrophoresis (Klee et al., 1979, Proc. Natl. Acad. Sci. USA 76:6270). Indeed, when the EGTA eluent was subjected to SDS-PAGE beside a calmodulin standard (Sigma), the $M_r$ 17,000 protein bands exhibited the $Ca_{2+}$-dependent gel mobility shift characteristic of calmodulin. Thus, the $M_r$ 17,000 protein is most likely calmodulin.

These results supported the possibility that the remaining three proteins could be part of a multi-subunit complex of calmodulin binding proteins, such as a $Ca^{2+}$, calmodulin-dependent kinase or $Ca^{2+}$, calmodulin-dependent phosphatase. Calcineurin is composed of two subunits, calcineurin A, a 61-kDa polypeptide, and calcineurin B, a 19-kDa polypeptide. As the 19-kDa calcineurin B migrates at about 15-kDa on SDS-PAGE, the $M_r$ 61,000 and 15,000 proteins could be calcineurin A and B respectively. It was also known that calcineurin A undergoes proteolysis to yield a 57-kDa protein.

When the four target protein bands were blotted onto PVDF membranes and subjected to N-terminal sequencing, they were all found to be N-terminally blocked. This is in agreement with the fact that both subunits of calcineurin, the 57-kDa proteolytic fragment of calcineurin A, and calmodulin have covalent modifications of their N-termini (Klee et al., 1988, supra, Aitken et al., 1984, Eur. J. Biochem. 139:663; Klee and Vanaman, 1982, Adv. Prot. Chem. 35:213). More importantly, 25- and 20-amino acid tryptic fragments derived from the $M_r$ 61,000 and 15,000 proteins obtained from the affinity experiments were sequenced by automated Edman degradation and shown to be 100% identical to sequences in calcineurin A Ser Gln Thr Thr Gly Phe Pro Ser Leu Ile Thr Ile Phe Ser Ala Pro Asn Tyr Leu Asp Val Tyr Asn Asn Lys. (Sequence I.D. No. 4) and calcineurin B Ile Tyr Asp Met Asp Lys Asp Gly Tyr Ile Ser Asn Gly Glu Leu Phe Gln Val Leu Lys. (Sequence I.D. No. 5), respectively.

Calcineurin B is a calcium binding protein with four $Ca^{2+}$-binding "EF" hands (Aitken et al., 1984, supra) and, like calmodulin, exhibits a gel mobility shift in the presence of calcium during SDS-PAGE. The $M_r$ 15,000 EGTA-eluted protein migrated faster in the presence of calcium. It was also found to comigrate with a calcineurin B standard (Sigma) in the presence or absence of calcium. The $M_r$ 61,000 and $M_r$ 57,000 EGTA-eluted proteins comigrate with a calcineurin A standard (Sigma), which do not undergo a gel-mobility shift in the presence of $Ca^{2+}$.

A western blot of the EGTA eluant from calf thymus with polyclonal antibodies against bovine brain calcineurin further established that the $M_r$ 61,000, 57,000, and 15,000 proteins are calcineurin A, a proteolytic fragment of calcineurin A, and calcineurin B, respectively. A $^{45}Ca^{2+}$ ligand blotting experiment with the EGTA eluant further supports the identify of the 15-kDa protein as calcineurin B. The weaker response of calmodulin ($r$ 17,000) was anticipated as it is known that under the same blotting conditions calmodulin provides a weaker signal.

Western blots of calcineurin, gel mobility shift of calmodulin and calcineurin B, and detection of calcineurin B by $^{45}Ca$ autoradiography were performed as follows.

For the Western blot of calcineurin A and B, the proteins were subjected to 12% SDS-PAGE followed by electroblotting onto nitrocellulose using a Bio-Rad Mini-blotting apparatus. Development of the blot with rabbit anti-calcineurin IgG and alkaline phosphatase conjugated goat-anti-rabbit IgG was performed as previously described (Burnette, 1981, Anal. Biochem. 112:195). To detect the calcium-dependent gel mobility shift of calmodulin and calcineurin B, $Ca^{2+}$, (1 mM) or EGTA (5 mM were added to the protein solution in SDS sample loading buffer before loading the gel. The $^{45}Ca^{2+}$-binding to calcineurin B and calmodulin and subsequent autoradiography were carried out as previously described (Maruyama et al., 1984, J. Biochem. 95:511). The $^{45}Ca^{2+}$ was purchased from New England Nuclear (Cambridge, Mass.).

Experiment 6

Calcineurin Binds to FKBP-FK506 and Cyclophilin-CsA in a $Ca^{2+}$-Dependent Fashion, and its Phosphatase Activity Towards a Phosphopeptide Substrate is Specifically Inhibited by the Two Immunophilin-Drug Complexes The binding between calcineurin and the immunophilin-drug complexes was studied with calcineurin purified from bovine brain. Calcineurin was found to be retained by GFK-FK506, but not GFK, or GFK-rapamycin. Since calmodulin was precipitated together with calcineurin from bovine brain and thymus extracts, it remained to be established whether the FKBP-FK506 complexes bind to calcineurin or calmodulin, and whether binding requires the prior formation of the calcineurin-calmodulin complex. These questions were addressed by experiments that demonstrated that the GFK-FK506 complex binds directly to calcineurin in the presence of $Ca^{2+}$ without calmodulin, and that the binding is dependent on $Ca^{2+}$ and $Mg^{2+}$. In the presence of calmodulin, however, increased amounts of calcineurin (both A and B subunits) appear to be adsorbed by the same amount of GFK-FK506 complex, and calmodulin is retained as well. The binding of calcineurin-calmodulin by GFK-FK506 was abolished by EGTA. Calmodulin alone does not bind to the GFK-FK506 complex in the presence of calcium.

Calcineurin is known to be a $Ca^{2+}$, calmodulin-dependent protein phosphatase (Stewart et al., 1982, FEBS. Lett. 137:80). Using a phosphorylated peptide fragment from the regulatory subunit of cAMP-dependent kinase as a substrate, the phosphatase activity of the calcineurin was assayed in the presence of the immunophilins, the individual drugs, and their respective complexes with or without calmodulin. Both the intrinsic $Ca^{2+}$-dependent and $Ca^{2+}$, calmodulin-stimulated phosphatase activities of calcineurin are potently inhibited by FKBP12-FK506 and cyclophilin A-CsA complexes, in agreement with the glutathione Sepharose adsorption experiments. It is worth noting that complexes of FKBP-rapamycin and FKBP-506BD do not significantly inhibit the phosphatase activity, in full agreement with the competitive binding assay and the previous observations that rapamycin inhibits different, calcium-independent signaling pathways and that 506BD, although a potent rotamase inhibitor of FKBP12, does not inhibit TCR-mediated signaling.

Calcineurin phosphatase assays were carried out essentially as described previously (Manalan et al. 1983, Proc. Natl. Acad. Sci. USA 80:4291) with minor modifications. The substrate used was a synthetic peptide corresponding to the phosphorylation site of the RII subunit of cyclic AMP-dependent protein kinase Asp Leu Asp Val Pro Ile Pro Gly Arg Phe Asp Arg Arg Val Ser Val Ala Ala Glu. (Sequence I.D. No. 1), which was phosphorylated with $^{32}p$-labeled ATP at the serine residue. The assay buffer consists of 40 mM TrisHCl (pH 7.5), 0.1 M NaCl, 6 mM $MgCl_2$, 0.1 mM $CaCl_2$, 0.1 mg/mL bovine serum albumin, and 0.5 mM dithiothreitol. The assay mixture (60 $\mu$l) contained 40 nM calcineurin, and 80 nM calmodulin (when present), and 2 $\mu$M phosphopeptide in addition to the assay buffer. It was found that the presence of methanol (3%) inhibits the phosphatase activity significantly. Therefore, the drug solutions were prepared in DMSO as follows. DMSO stock solutions of the drugs were prepared (3000×final concentration) and then diluted 100×with the assay buffer. 2 $\mu$L was added to the incubation mixture giving a final concentration of DMSO of less than 0.04% in the final assay mixture. The incubations were carried out at 30° C. for 10 min before the reaction was stopped by addition of the stop solution (5% trichloroacetic acid, 0.1 M potassium phosphate) and loaded onto 0.5 ml Dowex AG 50W-X8 (200-800 mesh, Bio-Rad) columns. After the [$^{32}P$]-inorganic phosphate was eluted from the column, it was mixed with 12 ml of ScintiVerse II (Fisher Scientific) and counted on a Beckman LS1801 Liquid Scintillation Systems. Bovine brain calcineurin and calmodulin were purchased from Sigma Chemical (St. Louis, Mo.). $^{32}P$-labeled phosphorylated peptide substrate, bovine brain calcineurin, and rabbit anti-calcineurin IgG were generous gifts from Dr. Claude B. Klee (National Cancer Institute, Department of Biochemistry). Goat-anti-rabbit IgG conjugated with alkaline phosphatase and the alkaline phosphatase substrates (BCIP and NBT) were obtained from Pierce (Rockford, ILL.). Glutathione Sepharose 4B was from Pharmacia LKB (Uppsala, Sweden). 506BD was prepared by Thomas J. Wandless and Patricia K. Somers in the Harvard laboratory.

Use

The methods of the invention can be used to treat an animal, e.g., a human, suffering from a condition characterized by a weakened immune response, e.g., AIDS. Dosages will vary based on factors known to those skilled in the art, e.g., the condition of the patient, the potency of the treatment, and the desired therapeutic effect.

Other Embodiments

Other embodiments are within the following claims, e.g., the affinity of immunosuppressive agents or immunosuppressive agent-immunophilin complexes for calcineurin can be used to identify and purify new immunosuppressive agents and immunophilins. Calcineurin could be immobilized on a solid state matrix and contacted with a sample containing a complex of an immunosuppressive agent and an immunophilin to purify the complex. The components of the complex could subsequently be separated and purified.

A specific immunosuppressive agent, e.g., CsA or FK506, could be added to a sample to allow the formation of complexes between the added immunosuppressive agent and an immunophilin in the sample. Likewise an immunophilin could be added to a sample to form complexes with an immunosuppressant in the sample.

The immunosuppressive activity of a compound can be determined by the ability of a complex containing the compound and an immunophilin, e.g., cyclophilin or FKBP, to bind to calcineurin, or by the ability of the complex to alter the phosphatase activity of calcineurin. Likewise the immunophilin-activity of a compound can be determined by the ability of a complex containing the compound and an immunosuppressant, e.g., FK506 or CsA, to bind to calcineurin, or by the ability of the complex to alter the phosphatase activity of calcineurin.

The ability of immunosuppressive compounds to bind to calcineurin or to alter the phosphatase activity of calcineurin can be used to purify or isolate the compounds. Purification or isolation can be based directly on the affinity of the compounds for calcineurin or on the use of binding or phosphatase activity as an assay for the presence of the compounds.

---

What is claimed is:

1. A method of evaluating the immunosuppressive activity of a compound comprising contacting said compound with calcineurin, contacting said compound-contacted-calcineurin with a phosphorylated substrate and determining the ability of said compound-contacted-calcineurin to dephosphorylate said substrate wherein the ability of said compound to decrease the phosphatase activity of said calcineurin being correlated to the immunosuppressant activity of said compound.

* * * * *